US012059269B2

(12) United States Patent
Mou et al.

(10) Patent No.: US 12,059,269 B2
(45) Date of Patent: Aug. 13, 2024

(54) WEARABLE DEVICE USED FOR DETECTION OF CARDIOVASCULAR SYSTEM OF USER

(71) Applicant: MICROJET TECHNOLOGY CO., LTD., Hsinchu (TW)

(72) Inventors: Hao-Jan Mou, Hsinchu (TW); Yung-Lung Han, Hsinchu (TW); Chi-Feng Huang, Hsinchu (TW); Tsung-I Lin, Hsinchu (TW); Chang-Yen Tsai, Hsinchu (TW); Wei-Ming Lee, Hsinchu (TW)

(73) Assignee: MICROJET TECHNOLOGY CO., LTD., Hsinchu (TW)

( * ) Notice: Subject to any disclaimer, the term of this patent is extended or adjusted under 35 U.S.C. 154(b) by 718 days.

(21) Appl. No.: 17/136,248

(22) Filed: Dec. 29, 2020

(65) Prior Publication Data
US 2021/0204881 A1 Jul. 8, 2021

(30) Foreign Application Priority Data
Jan. 7, 2020 (TW) .................. 109100513

(51) Int. Cl.
*A61B 5/00* (2006.01)
*A61B 5/021* (2006.01)
(Continued)

(52) U.S. Cl.
CPC ........ *A61B 5/6843* (2013.01); *A61B 5/02233* (2013.01); *A61B 5/02255* (2013.01);
(Continued)

(58) Field of Classification Search
CPC .............. A61B 5/6843; A61B 5/02233; A61B 5/02255; A61B 5/0235; A61B 5/02422;
(Continued)

(56) References Cited

U.S. PATENT DOCUMENTS 8,105,057 B2 * 1/2012 Chen ..................... F04B 43/046
417/413.1
9,611,843 B2 * 4/2017 Hsueh .................. F04B 43/046
(Continued)

FOREIGN PATENT DOCUMENTS

| CN | 204394491 U | 6/2015 |
|---|---|---|
| CN | 105979854 A | 9/2016 |

(Continued)

*Primary Examiner* — Alex M Valvis
*Assistant Examiner* — Justin Xu
(74) *Attorney, Agent, or Firm* — Birch, Stewart, Kolasch & Birch, LLP

(57) ABSTRACT

A wearable device for measuring a cardiovascular system of a user includes an attachment component, a blood pressure measurement module, and a sensor configured to detect an existence of a limb part of the user. The attachment component is for attaching the wearable device to the limb part of the user and includes a connecting mechanism. A condition of the connecting mechanism can be used to determine whether the attachment component is in a connected configuration or in a disconnected configuration. The blood pressure measurement module has an expander, an actuator, and a blood pressure measurement sensor. The expander can be disposed on the limb part and can contact against the user. The expander can be controlled by the actuator to be inflated, by which the blood pressure measurement sensor can measure blood pressure in the cardiovascular system of the user.

13 Claims, 22 Drawing Sheets

(51) Int. Cl.
*A61B 5/022* (2006.01)
*A61B 5/0225* (2006.01)
*A61B 5/0235* (2006.01)
*A61B 5/024* (2006.01)
*A61B 5/026* (2006.01)
*A61B 5/0295* (2006.01)

(52) U.S. Cl.
CPC ........ *A61B 5/0235* (2013.01); *A61B 5/02422* (2013.01); *A61B 2560/0223* (2013.01); *A61B 2560/0266* (2013.01); *A61B 2562/0223* (2013.01); *A61B 2562/0257* (2013.01)

(58) Field of Classification Search
CPC .... A61B 2560/0223; A61B 2560/0266; A61B 2562/0223; A61B 2562/0257; A61B 5/02141; A61B 5/0261; A61B 5/0295; A61B 5/6824
See application file for complete search history.

(56) References Cited

U.S. PATENT DOCUMENTS

| | | | |
|---|---|---|---|
| 10,492,726 | B2 | 12/2019 | Dusan et al. |
| 2006/0011729 | A1 | 1/2006 | Sarela et al. |
| 2012/0136605 | A1* | 5/2012 | Addison ............... A61B 5/7221 702/98 |
| 2018/0325395 | A1* | 11/2018 | Chen ....................... F04B 39/10 |
| 2019/0002956 | A1 | 1/2019 | Stumbo et al. |
| 2019/0029596 | A1 | 1/2019 | Kang et al. |

FOREIGN PATENT DOCUMENTS

| | | |
|---|---|---|
| CN | 107007272 A | 8/2017 |
| CN | 107080531 A | 8/2017 |
| CN | 208610829 U | 3/2019 |
| CN | 109745023 A | 5/2019 |
| CN | 209252837 U | 8/2019 |
| CN | 209770339 U | 12/2019 |
| TW | 509054 U | 11/2002 |
| TW | M455472 U | 6/2013 |
| TW | M560881 U | 6/2018 |
| TW | M576726 U | 4/2019 |
| TW | M579275 U | 6/2019 |
| TW | M582825 U | 9/2019 |

\* cited by examiner

WEARABLE DEVICE USED FOR DETECTION OF CARDIOVASCULAR SYSTEM OF USER

CROSS-REFERENCE TO RELATED APPLICATION

This non-provisional application claims priority under 35 U.S.C. § 119(a) to Patent Application No. 109100513 in Taiwan, R.O.C. on Jan. 7, 2020, the entire contents of which are hereby incorporated by reference.

BACKGROUND

Technical Field

The present disclosure relates to a wearable device. In particular, to a wearable device for measuring the blood pressure in a cardiovascular system of a user.

Related Art

In recent years, awareness of personal health care has gradually increased so that the need of regularly monitoring the self-health condition has been generated. However, since most of the instruments for examining the body health condition are stationary facility, and people have to go to a medical service station or a hospital to obtain their health examination information. Even if there are already some detection devices for household uses on the market, sizes of these devices are still too large to be carried easily. In the current efficiency-pursuing society, these detection devices are hard to satisfy the needs of users.

Among the various health related indexes, the most representative one should be the blood pressure. The blood vessels in one's body are like roads spreading all over the body. Thus, the blood pressure is just like the road conditions, and the condition of the blood delivery can be understood through the blood pressure. If anything happens to the body, the blood pressure will reflect it clearly.

In view of these, how to provide a device capable of accurately measuring the blood pressure of a user, combined with a wearable electronic device or a portable electronic device so that the user can quickly check the blood pressure whenever and wherever with the device is an issue raised currently.

SUMMARY

In general, one of the objects of the present disclosure is to provide a wearable device for measuring the blood pressure in the cardiovascular system of a user, so that the user can carry the wearable device conveniently and can measure/monitor the blood pressure of a limb part of the user. Through an expander of the wearable device, the tightness between the user's skin and the wearable device can be adjusted according to different usage scenarios. For example, during measuring the blood pressure, the expander is inflated and close-fits against the user's limb part. When the wearable device is not in the measuring mode, the expander does not inflate and thus provides more comfortable wearing experience. Moreover, by using a photoplethysmography (PPG) sensor accompanied with a blood pressure measurement module through the inflated blood pressure measurement method, the calculation for the basis initial calibration of the blood pressure obtained by the photo-plethysmography sensor can be performed. Thus, the photo-plethysmography sensor can measure with accurate blood pressure value at any time.

To achieve the above mentioned purpose(s), a general embodiment of the present disclosure provides a wearable device, for measuring the blood pressure of the cardiovascular system of a user, and the wearable device is operable in a connected state and a disconnected state. The wearable device includes an attachment component for attaching the wearable device to a limb part of the user, a blood pressure measurement module, and a sensor for detecting the limb part of the user. The attachment component includes a connecting mechanism for determining whether the attachment component is in a connected configuration or in a disconnected configuration. The blood pressure measurement module has an expander, an actuator, and a blood pressure measurement sensor. The expander is capable of being disposed on the limb part and contacting the user in a non-invasive manner. The expander is in communication with the actuator through a ventilation channel. The expander is capable of being controlled by the actuator to be inflated, and enable the blood pressure measurement sensor to measure a blood pressure or a pulse in the cardiovascular system of the user. The blood pressure measurement sensor is used for measuring the blood pressure at the limb part of a user. The wearable device is switched to the connected state from the disconnected state when the attachment component is detected to be connected to the wearable device. The attachment component is capable of being switched between the connected configuration and the connected configuration. The wearable device would detect when is the attachment component switched from the disconnected configuration to the connected configuration. The wearable device operating under the disconnected state would checks whether the sensor detects the blood pressure at limb part of the user when the attachment component is switched from the disconnected configuration to the connected configuration.

BRIEF DESCRIPTION OF THE DRAWINGS

The disclosure will become more fully understood from the detailed description given herein below for illustration only, and thus not limitative of the disclosure, wherein.

DETAILED DESCRIPTION

The present disclosure will now be described more specifically with reference to the following embodiments. It is to be noted that the following descriptions of different embodiments of this disclosure are presented herein for purpose of illustration and description only, and it is not intended to limit the scope of the present disclosure.

Figure 1:
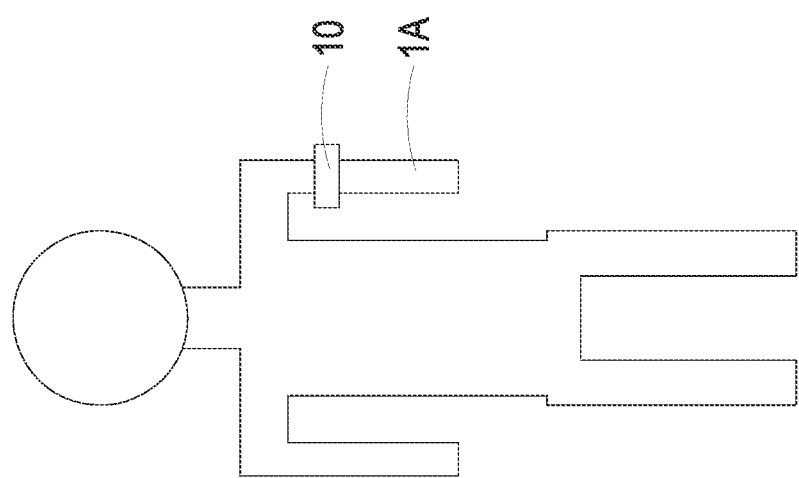
FIG. 1 illustrates a schematic view of a wearable device worn on a limb part of a user according to an exemplary embodiment of the present disclosure.
Figure 2A:
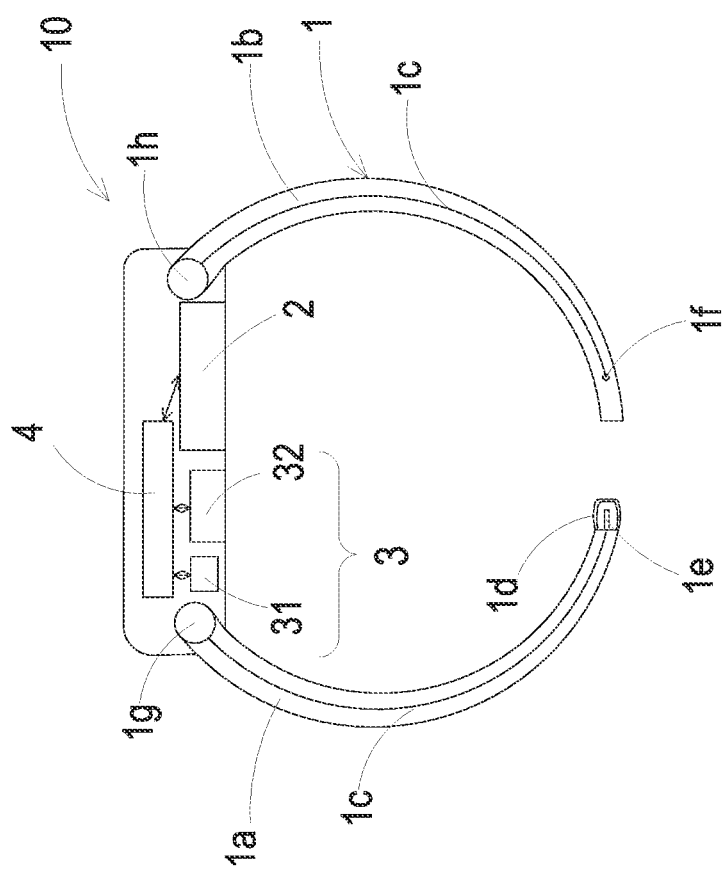
FIG. 2A illustrates a schematic view showing the component assembly relationship of a wearable device according to a first embodiment of the present disclosure, wherein the attachment component is in a disconnected configuration.

Please refer to FIG. 1 and FIG. 2A. The present disclosure provides a wearable device 10 for measuring blood pressure in a cardiovascular system of a user. The user has a limb part 1A, and the wearable device 10 can be operated in a connected state or a disconnected state. The wearable device 10 mainly includes an attachment component 1, a blood pressure measurement module 2, a sensor 3, and a processor 4. The attachment component 1 may have a connected configuration and a disconnected configuration. The wearable device 10 is configured to be operated in the connected state when the attachment component 1 is attached to the user's limb part 1A, while the wearable device 10 is configured to be operated in the disconnected state when the attachment component 1 is not attached to the user's limb part 1A. If the wearable device 10 is in the connected state and the attachment component 1 is switched from the connected configuration to the disconnected configuration, the wearable device 10 will be switched to the disconnected state responsively. On the other hand, when the wearable device 10 is in the disconnected state and the attachment component 1 is switched from the disconnected configuration to the connected configuration, the wearable device 10 will determine if it is worn by the user depending on whether the sensor 3 detects the user's limb part 1A. If the sensor 3 detects the user's limb part 1A, then the sensor 3 will switch the wearable device 10 to the connected state.

Figure 2B:
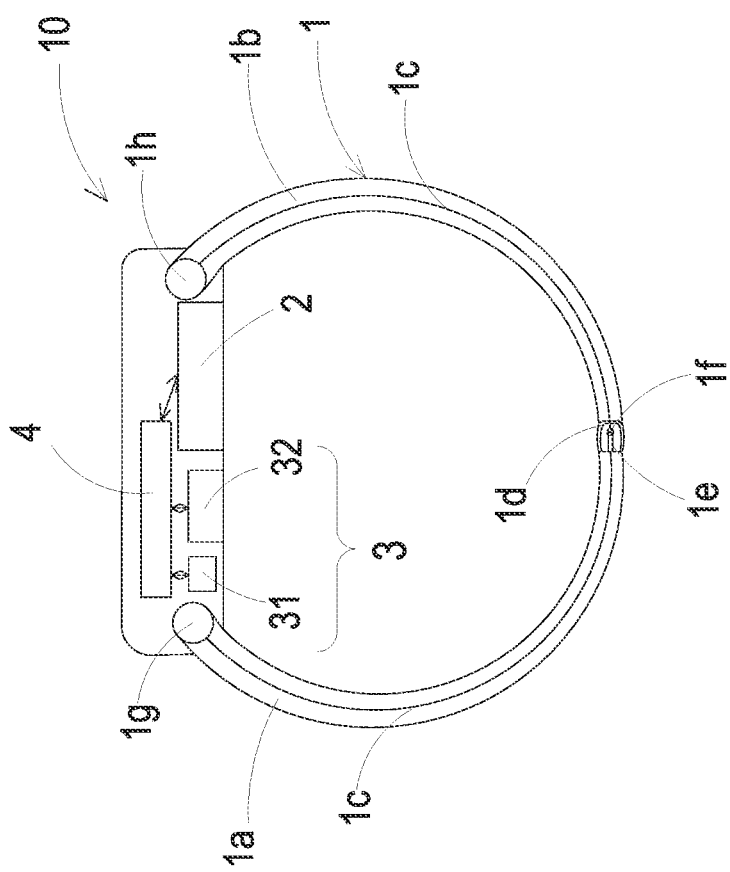
FIG. 2B illustrates a schematic view showing the component assembly relationship of the wearable device in FIG. 2A, wherein the attachment component is in a connected configuration.

The above mentioned attachment component 1 can attach the wearable device 10 to the user's limb part 1A. By measuring the conductivity coefficient or the current between two or more contacts in the attachment component 1 of the wearable device 10, the wearable device 10 can determine whether the attachment component 1 is in the connected configuration or in the disconnected configuration. As shown in FIG. 2A and FIG. 2B, in the first embodiment of the present disclosure, the attachment component 1 for attaching the wearable device 10 to the user's limb part 1A may include a first portion 1a, a second portion 1b, a conductive element 1c, and a connecting mechanism. The connecting mechanism of this embodiment includes a buckle 1d, a conductive pin 1e, and a conductive hole 1f, and the connecting mechanism is configured to determine whether the attachment component 1 is in the connected configuration or in the disconnected configuration. The conductive element 1c of the first portion 1a is electrically connected to a first contact 1g and the conductive pin 1e, and the conductive element 1c of the second portion 1b is electrically connected to a second contact 1h and the conductive hole 1f. Thus, an electrical connection can be established between the first contact 1g and the second contact 1h when the first portion 1a and the second portion 1b together construct the connected configuration of the attachment component 1. That is, through electrically coupling the conductive pin 1e and the conductive hole 1f, the conductive elements 1c respectively in the first portion 1a and the second portion 1b can be electrically connected with each other, and thus the first contact 1g and the second contact 1h can be electrically connected with each other as well. Accordingly, the processor 4 can determine that the attachment component 1 is in the connected configuration. On the other hand, when the first portion 1a and the second portion 1b are separated apart, the circuit in the attachment member 1 is open. Therefore, the configuration of the attachment component 1 (or the condition between the first portion 1a and the second portion 1b) can be determined through measuring the conductivity coefficient between the first contact 1g and the second contact 1h.

Figure 3A:
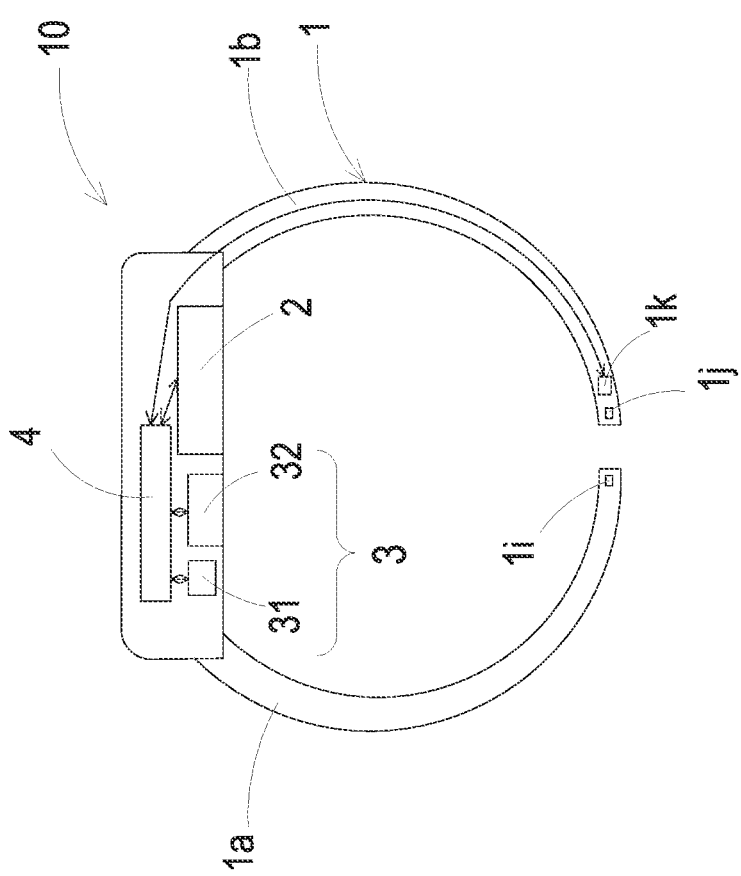
FIG. 3A illustrates a schematic view showing the component assembly relationship of a wearable device according to a second embodiment of the present disclosure, wherein the attachment component is in a disconnected configuration.
Figure 3B:
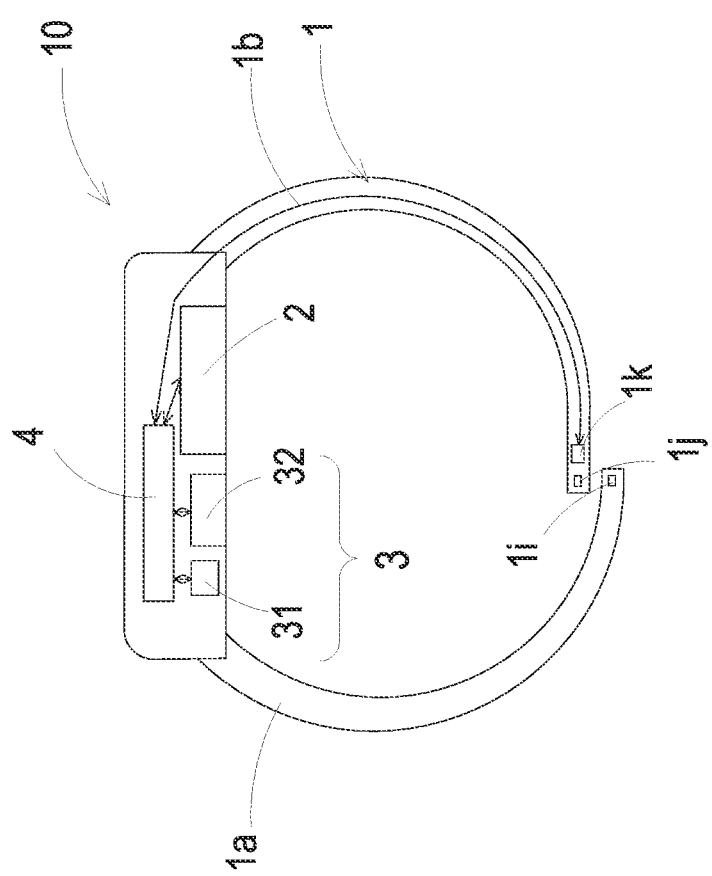
FIG. 3B illustrates a schematic view showing the component assembly relationship of the wearable device in FIG. 3A, wherein the attachment component is in a connected configuration.

Please then refer to FIG. 3A and FIG. 3B. In the second embodiment of the present disclosure, the connecting mechanism of the attachment component 1 may include a first magnetic element 1i located in the first portion 1a and a second magnetic element 1j located in the second portion 1b. FIG. 3A illustrates a schematic side view showing the component relationship of the wearable device 10 according to the second embodiment of the present disclosure, and the attachment component 1 is in the disconnected configuration. The attachment component 1 can be switched to the connected configuration shown in FIG. 3B through coupling the first magnetic element 1*i* located in the first portion 1*a* to the second magnetic element 1*j* located in the second portion 1*b*. Conversely, the connection configuration shown in FIG. 3B can be switched to the disconnected configuration shown in FIG. 3A by disengaging the first magnetic element 1*i* and the second magnetic element 1*j* in the first portion 1*a* and the second portion 1*b*, respectively. Moreover, the attachment component 1 may further include a Hall-effect sensor 1*k* or other kinds of sensor for measuring the magnetic fields of the first magnetic element 1*i* and the magnetic field of the second magnetic element 1*j*, and the sensor is communicationally connected to the processor 4. Therefore, through measuring the magnetic field of the first magnetic element 1*i* and the magnetic field of the second magnetic element 1*j*, whether the attachment component 1 is in the connected configuration or in the disconnected configuration can be determined.

Figure 4A:
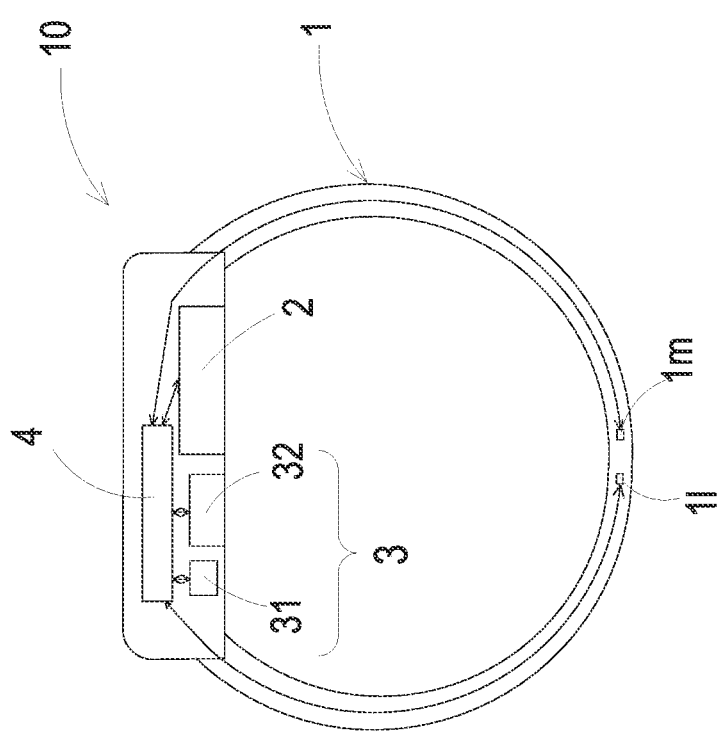
FIG. 4A illustrates a schematic view showing the component assembly relationship of a wearable device according to a third embodiment of the present disclosure, wherein the attachment component is in a connected configuration.
Figure 4B:
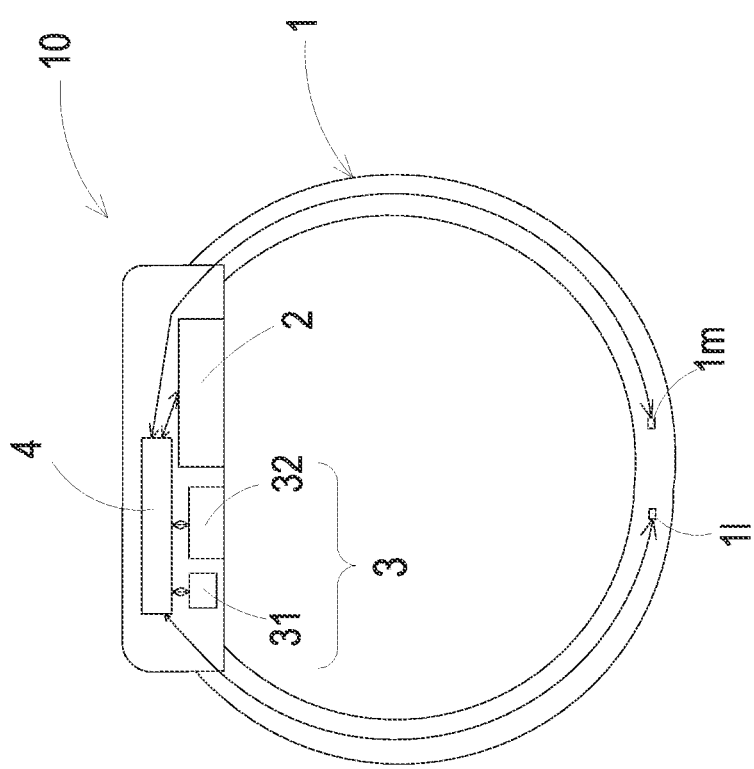
FIG. 4B illustrates a schematic view showing the component assembly relationship of the wearable device in FIG. 4A, wherein the attachment component is stretched.

Please refer to FIG. 4A and FIG. 4B. In the third embodiment of the present disclosure, the attachment component 1 may include a first capacitive element 1*l* and a second capacitive element 1*m*, which are communicationally connected to the processor 4. The capacitance between the first capacitive element 1*l* and the second capacitive element 1*m* is changed according to the changes of the distance between the first capacitive element 1*l* and the second capacitive element 1*m* when the attachment component 1 is stretched or not stretched. Specifically, in this embodiment, the capacitance is relatively greater when the attachment component 1 is not stretched (as shown in FIG. 4A); and relatively smaller when the attachment component 1 is stretched (as shown in FIG. 4B). Thus, whether the attachment component 1 is in the connected configuration or in the disconnected configuration can be determined through measuring the change of the capacitance.

The sensor 3 mentioned above may include a photoplethysmography (PPG) sensor 31 and a proximity sensor 32, which are embedded in the wearable device 10 for detecting and/or measuring the blood pressure in the limb part 1A of the user. The proximity sensor 32 can be used to determine whether the attachment component 1 of the wearable device 10 is in the connected configuration or in the disconnected configuration. Specifically, in this embodiment, when the proximity sensor 32 detects the existence of the limb part 1A of the user, it represents that the attachment component 1 is in the connected configuration. While the proximity sensor 32 does not detect the existence of the limb part 1A of the user, it represents that the attachment component 1 is in the disconnected configuration. Therefore, the proximity sensor 32 can be used to determine when the attachment component 1 of the wearable device 10 is switched between the connected configuration and the disconnected configuration.

Figure 5A:
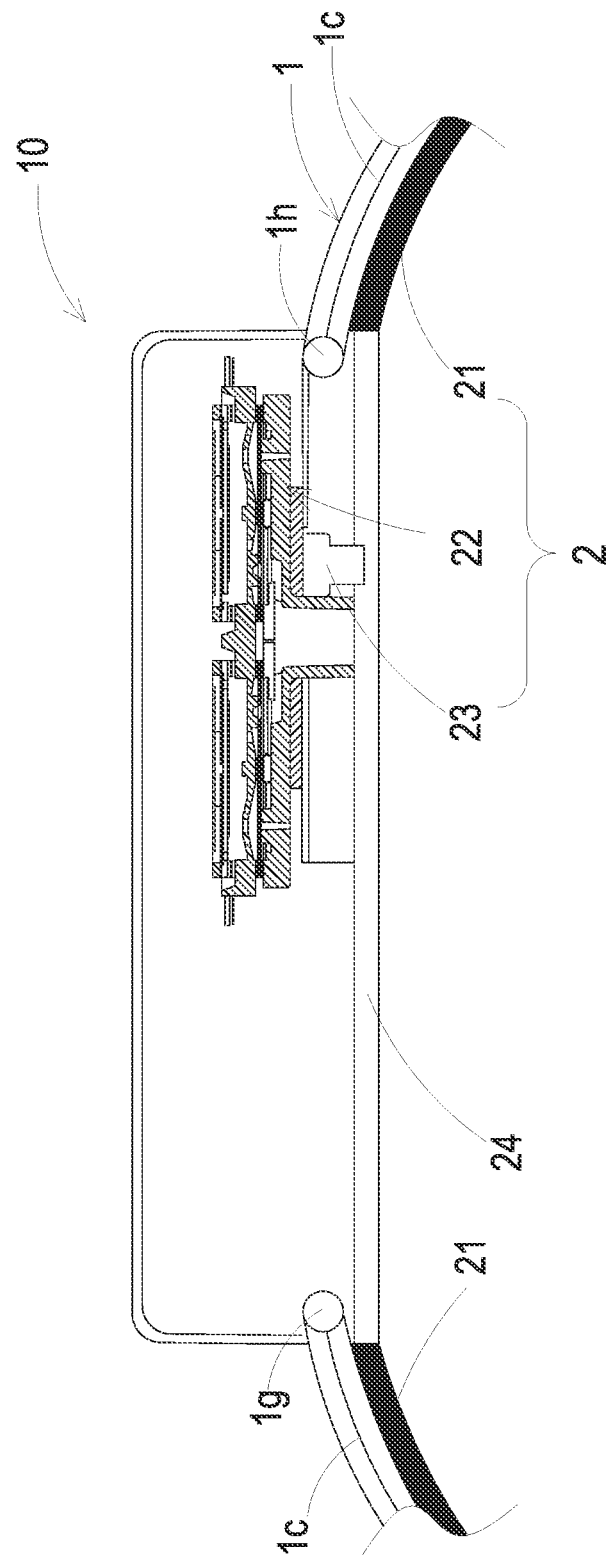
FIG. 5A illustrates a schematic cross-sectional view showing the component assembly relationship of a blood pressure measurement module in a wearable device according to an exemplary embodiment of the present disclosure.

Please refer to FIG. 5A. The above mentioned blood pressure measurement module 2 is embedded in the wearable device 10. The blood pressure measurement module 2 includes an expander 21, an actuator 22, and a blood pressure measurement sensor 23. The expander 21 is capable of being disposed on the limb part 1A and close-fitting against the user in a non-invasive way. Moreover, the expander 21 is capable of being controlled by the actuator 22 to be inflated, so that the blood pressure measurement sensor 23 can measure a blood pressure and pulse in the cardiovascular system of the user.

Figure 6:
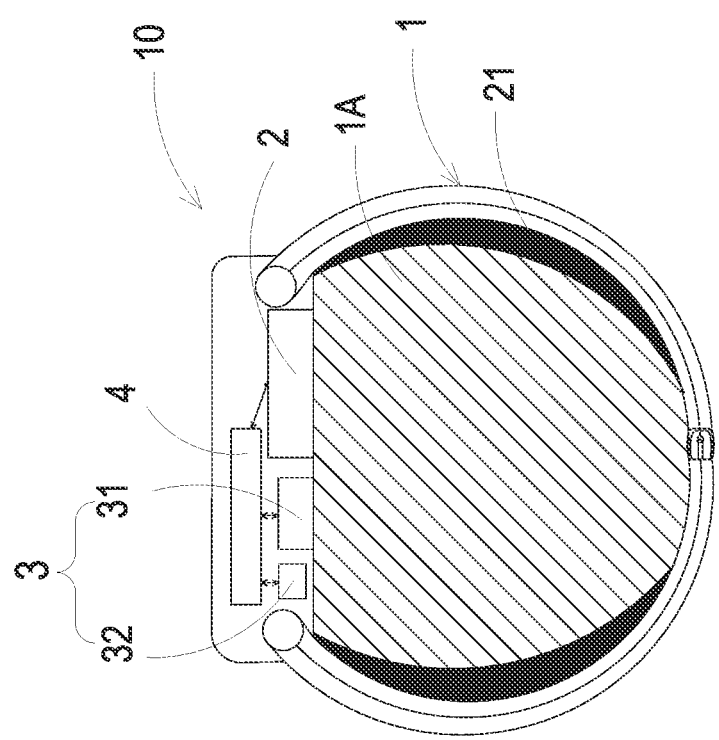
FIG. 6 illustrates a schematic cross-sectional view of the wearable device showing that the expander is inflated by the blood pressure measurement module to contact against the limb part of the user.

In some embodiments, the expander 21 mentioned above may be a gas bag made of an elastic material. The expander 21 may be disposed on the inner side of the attachment component 1 and shrinks to form a flat surface. The expander 21 is in communication with the actuator 22 through a ventilation channel 24, by which the expander 21 can be controlled by the actuator 22 to be inflated, so that the expander 21 can fit over and close-fit against the limb part 1A of the user (as shown in FIG. 6).

Figure 5B:
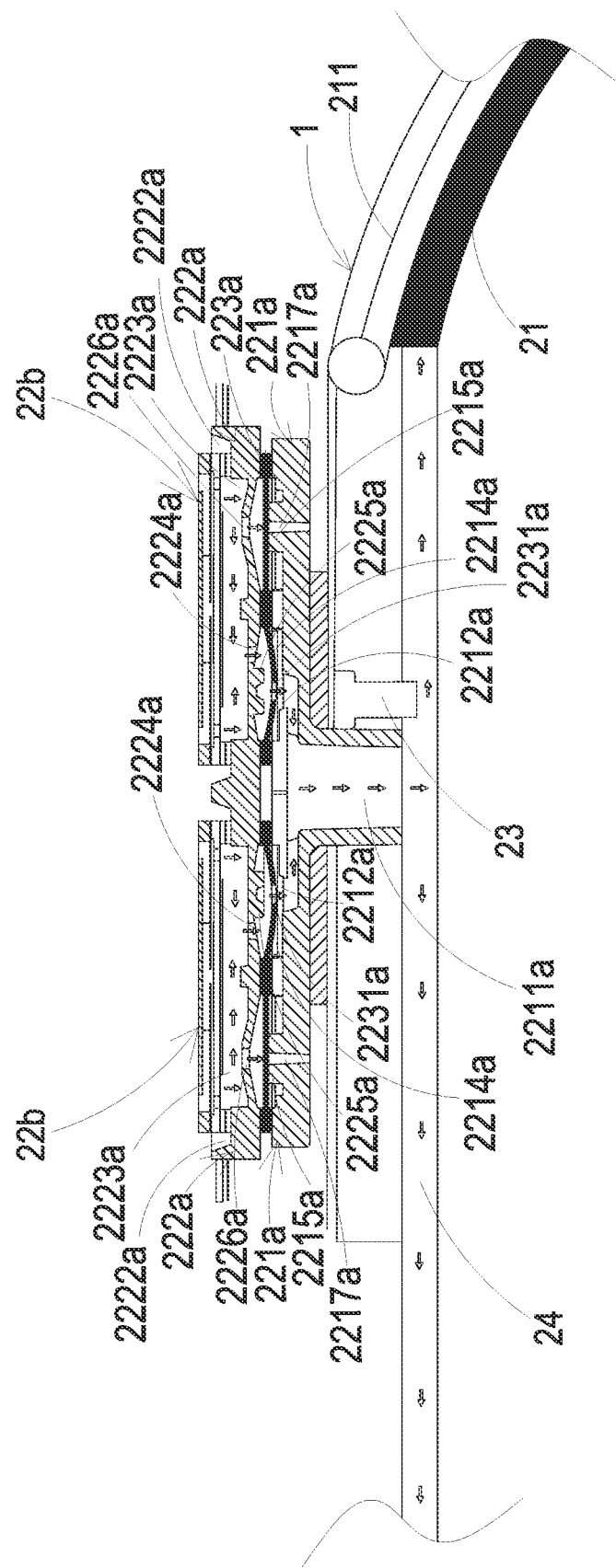
FIG. 5B illustrates a schematic cross-sectional view of the blood pressure measurement module during a gas converging process (inflating process)
Figure 7A:
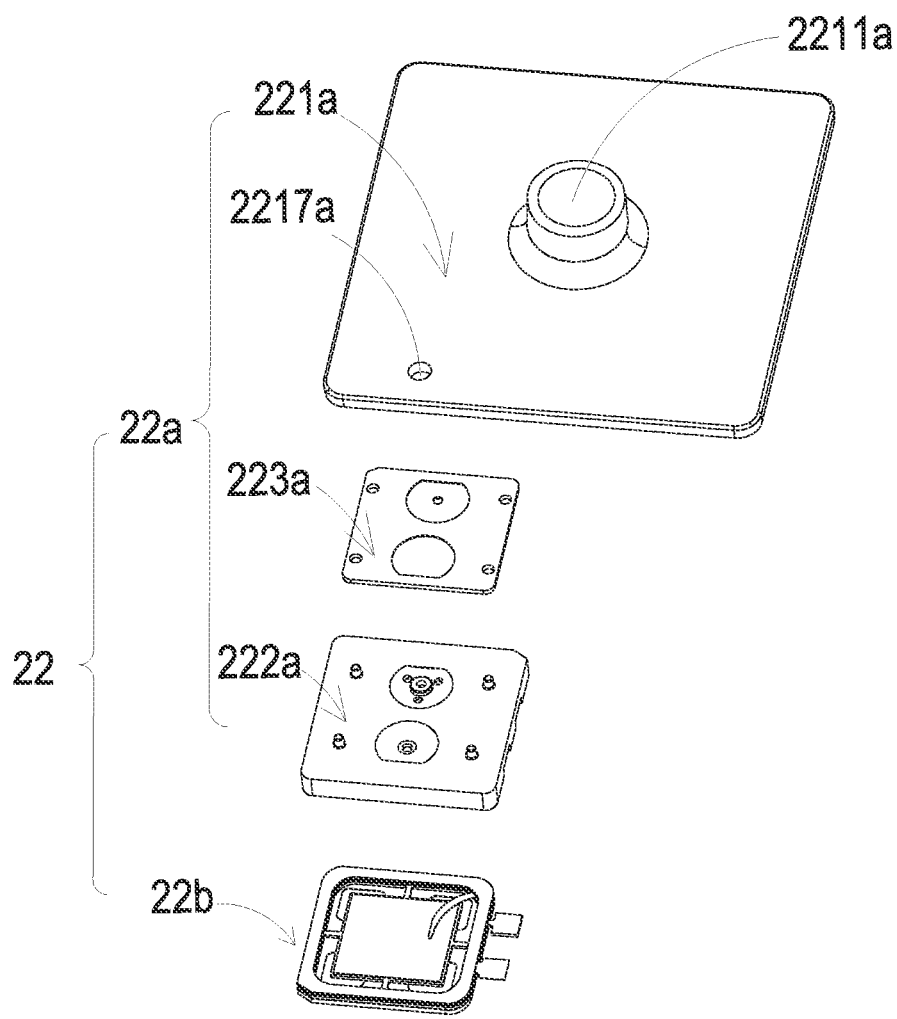
FIG. 7A illustrates a schematic exploded view of an actuator of the blood pressure measurement module according to the exemplary embodiment of the present disclosure.
Figure 7B:
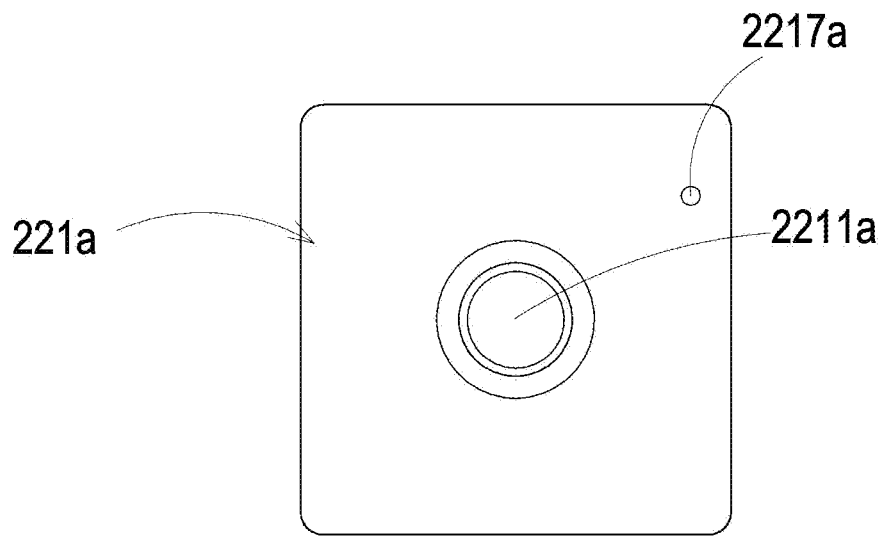
FIG. 7B illustrates a schematic top view of the convergence plate shown in FIG. 7A.
Figure 7C:
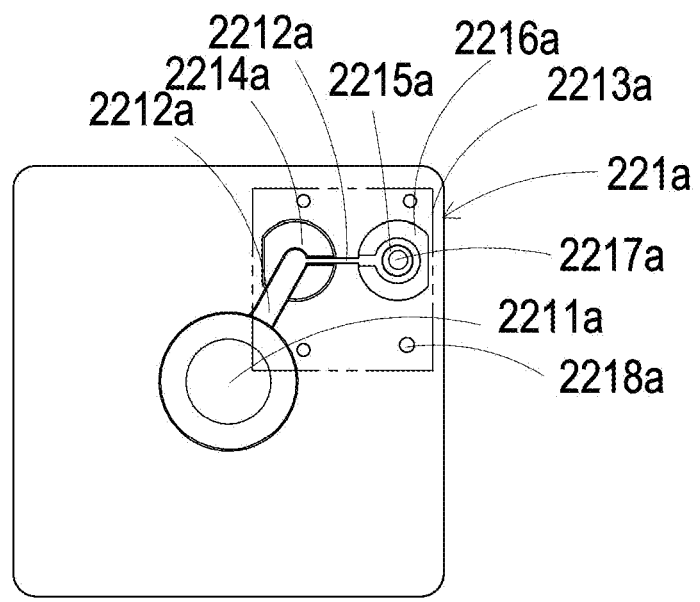
FIG. 7C illustrates a schematic bottom view of the convergence plate shown in FIG. 7A.

Please refer to FIG. 5B and FIG. 7A. The actuator 22 includes a valve device 22*a* and at least one gas transmission device 22*b*. In this embodiment, a plurality of the gas transmission devices 22*b* are disposed on one side of the valve device 22*a* and covers the one side of the valve device 22*a*. Thus, the valve device 22*a* and the plurality of the gas transmission devices 22*b* can be seen as one component. The valve device 22*a* includes a convergence plate 221*a*, at least one chamber plate 222*a*, and at least one valve sheet 223*a*. Please refer to FIG. 7B to FIG. 7C. A convergence outlet 2211*a* is disposed on the convergence plate 221*a* and penetrates the convergence plate 221*a* from one surface of the convergence plate 221*a* to the opposite surface of the convergence plate 221*a*. A plurality of convergence plate assembly areas 2213*a* are defined on one surface of the convergence plate 221*a*. The number of the convergence plate assembly areas 2213*a* disposed on the convergence plate 221*a* may correspond to the number of a component set (including one chamber plate 222*a*, one valve plate 223*a*, and one gas transmission device 22*b*) desired to be assembled on the convergence plate 221*a*, and can be modified as desired. In this embodiment, the actuator 22 has four convergence plate assembly areas 2213*a*, four chamber plates 222*a*, four valve sheets 223*a*, and four gas transmission devices 22*b*, but is not limited thereto. Moreover, each of the convergence plate assembly areas 2213*a* of the convergence plate 221*a* has a guiding channel 2212*a* in communication with the convergence outlet 2211*a*, a convergence trough 2214*a*, and a discharge trough 2216*a*. The guiding channel 2212*a* is served as a connecting passage between the convergence trough 2214*a* and the discharge trough 2216*a*, so that the convergence trough 2214*a* and the discharge trough 2216*a* communicate with each other through the guiding channel 2212*a*. Each of the convergence plate assembly areas 2213*a* has a convergence plate convex portion 2215*a* and a discharge outlet 2217*a*. The convergence plate convex portion 2215*a* is disposed in the discharge trough 2216*a*, and the convergence plate convex portion 2215*a* is surrounded by the discharge trough 2216*a*. The discharge outlet 2217*a* is disposed at the central portion of the convergence plate convex portion 2215*a*, and the discharge outlet 2217*a* penetrates the convergence plate 221*a* from one surface of the convergence plate 221*a* to the opposite surface of the convergence plate 221*a*. Accordingly, since the convergence plate assembly area 2213*a* of the convergence plate 221*a* covers the corresponding chamber plate 222*a*, the gas discharged out from the chamber plate 222*a* can be converged at the guiding channel 2212*a* of the convergence plate 221*a*. Then, the gas can be guided to the convergence outlet 2211*a* through the guiding channel 2212*a* and be discharged out afterwards. As shown in FIG. 7A, FIG. 7B, and FIG. 7C, in order to make the embodiment more clearly, only one set of a convergence plate assembly area 2213*a*, a chamber plate 222*a*, a valve sheet 223*a*, and a gas transmission device 22*b* are shown on the convergence plate 221*a* in these figures for illustrating the configuration relationship between different components. It should be noted that, in this embodiment, a plurality of convergence plate assembly areas 2213a can be defined on the convergence plate 221a and a plurality of discharge outlets 2217a can be disposed on the convergence plate 221a accordingly for discharging gas, but only one convergence outlet 2211a is disposed on the convergence plate 221a for converging gas. For example, if four sets of convergence plate assembly areas 2213a are disposed on the convergence plate 221a, four chamber plates 222a, four valve sheets 223a, and four gas transmission devices 22b would be arranged on the convergence plate 221a, but only one convergence outlet 2211a would be provided on the convergence plate 221a for converging gas. To this end, four discharge outlets 2217a would be disposed on the convergence plate 221a for discharging gas in each of the convergence plate assembly areas 2213a, respectively.

Figure 7D:
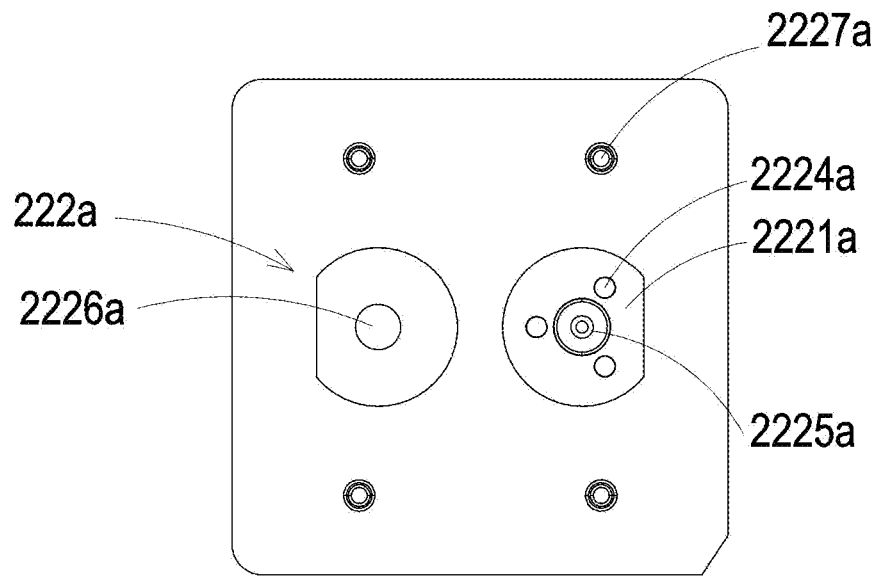
FIG. 7D illustrates a schematic top view of the chamber plate shown in FIG. 7A.
Figure 7E:
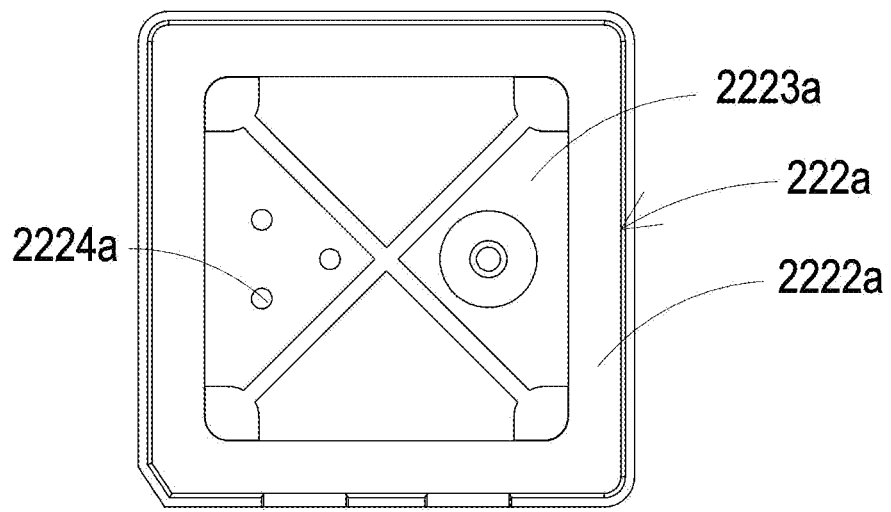
FIG. 7E illustrates a schematic bottom view of the chamber plate shown in FIG. 7A.

Please refer to FIG. 7D and FIG. 7E. One surface of the chamber plate 222a is recessed to form a flow guiding chamber 2221a. The opposite surface of the chamber plate 222a is recessed to form a receiving trough 2222a. The flow guiding chamber 2221a corresponds to the convergence trough 2214a of the convergence plate 221a and is in communication with the convergence trough 2214a. In other words, the flow guiding chamber 2221a and the receiving trough 2222a are respectively disposed on two opposite surfaces of the chamber plate 222a. A confluence chamber 2223a is disposed on a bottom of the receiving trough 2222a, and at least one communication hole 2224a is disposed on a bottom of the confluence chamber 2223a. The communication hole 2224a penetrates the chamber plate 222a so that the confluence chamber 2223a can communicate with the flow guiding chamber 2221a. In this embodiment, the number of the communication holes 2224a is three, but is not limited thereto. A chamber plate convex portion 2225a is disposed in the flow guiding chamber 2221a, and the communication holes 2224a are disposed around the chamber plate convex portion 2225a. A second communication hole 2226a is disposed on a portion of the chamber plate 222a corresponding to the discharge trough 2216a of each of the plurality of convergence plate assembly areas 2213a of the convergence plate 221a. The second communication hole 2226a penetrates the chamber plate 222a, and thus the second communication hole 2226a can communicate with the confluence chamber 2223a.

Figure 7F:
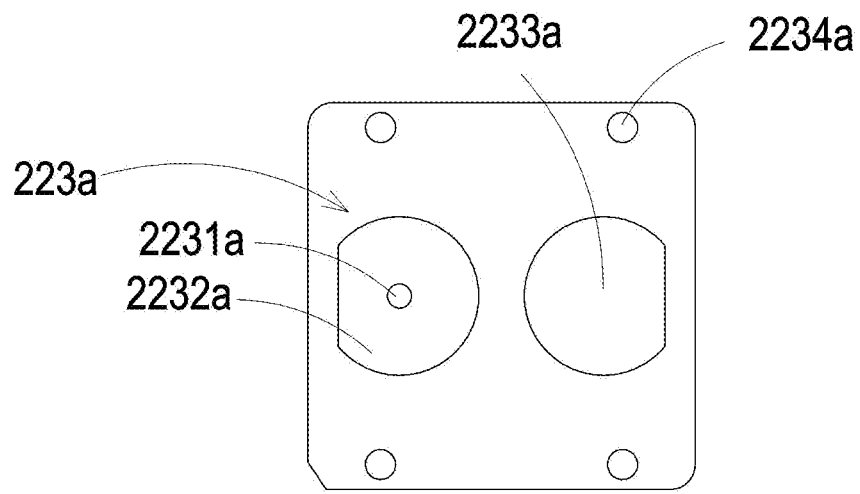
FIG. 7F illustrates a schematic top view of the valve sheet shown in FIG. 7A.
Figure 7G:
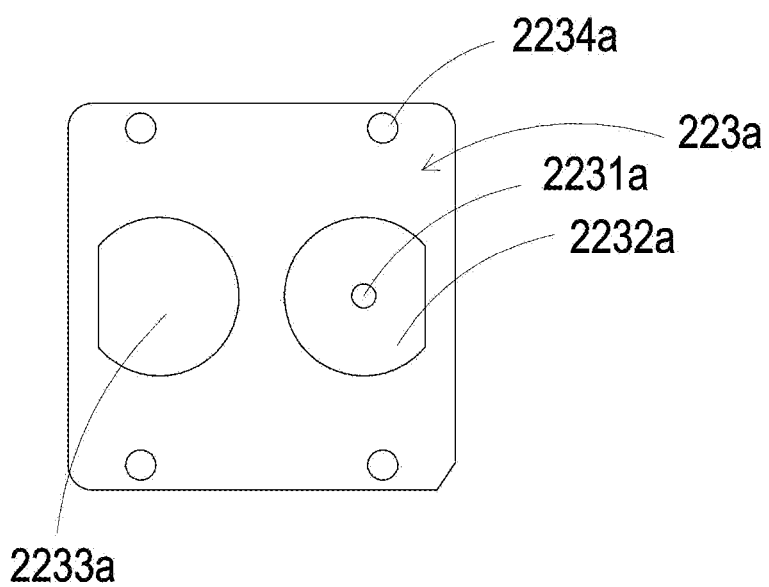
FIG. 7G illustrates a schematic bottom view of the valve sheet shown in FIG. 7A.
Figure 8A:
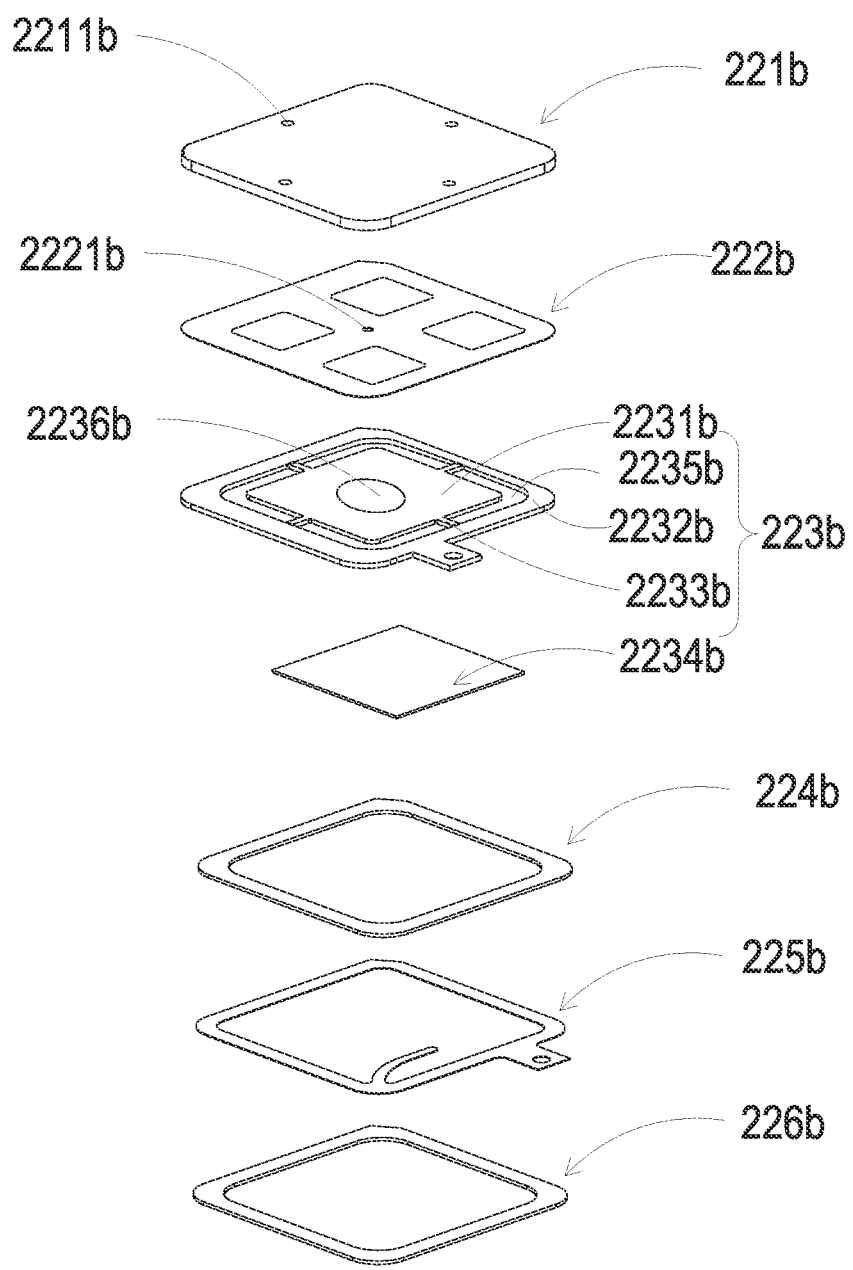
FIG. 8A illustrates a front exploded view of a gas transmission device in the blood pressure measurement module according to the exemplary embodiment of the present disclosure.
Figure 8B:
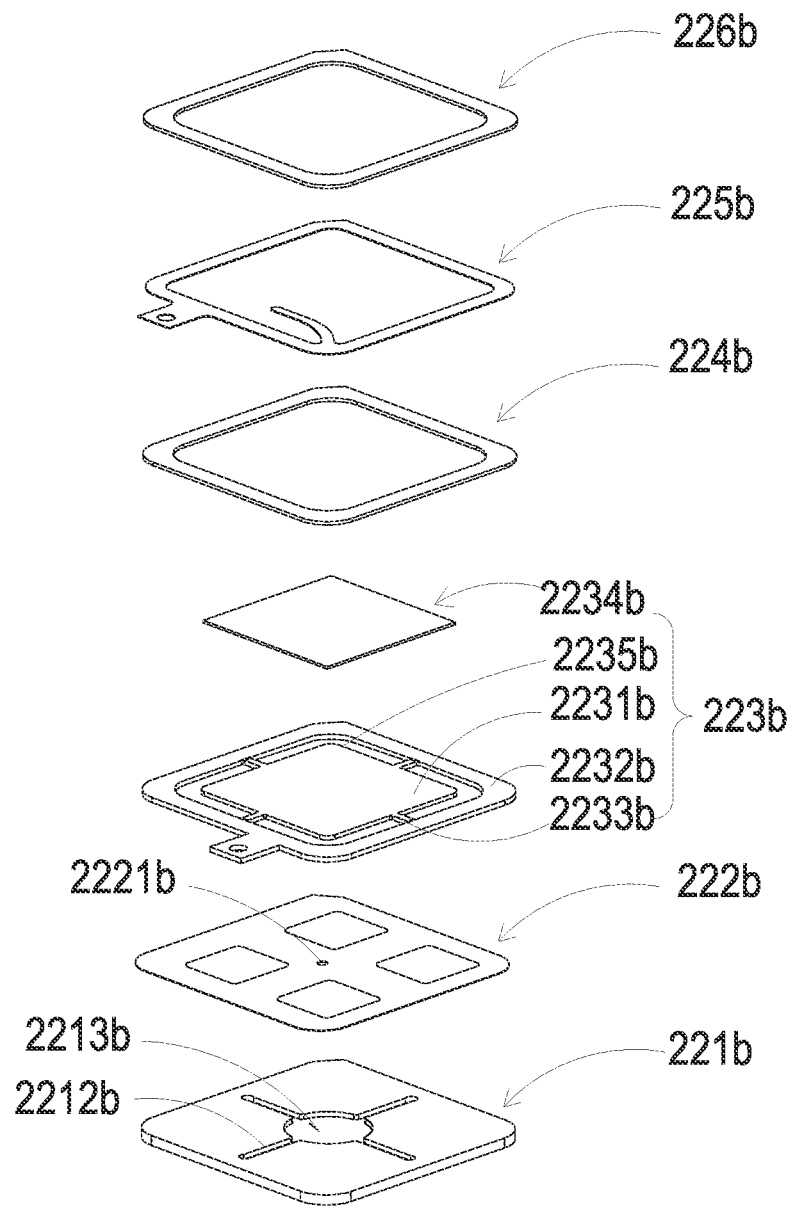
FIG. 8B illustrates a rear exploded view of the gas transmission device in the blood pressure measurement module according to the exemplary embodiment of the present disclosure.

Please refer to FIG. 7F and FIG. 7G The valve sheet 223a is disposed between the convergence plate 221a and the chamber plate 222a. When the valve sheet 223a is disposed and positioned on one surface of the chamber plate 222a, a valve hole 2231a is disposed on the valve sheet 223a and corresponds to the chamber plate convex portion 2225a, and thus the valve hole 2231a is sealed by the chamber plate convex portion 2225a. Moreover, when the convergence plate 221a is disposed and positioned on the valve sheet 223a, the valve sheet 223a correspondingly abuts against the convergence plate convex portion 2215a in the convergence plate assembly area 2213a. Moreover, in this embodiment, a convergence concave sheet 2232a and a discharge concave sheet 2233a are disposed between the two opposite contact surfaces of the valve sheet 223a. The convergence concave sheet 2232a correspondingly abuts against the chamber plate convex portion 2225a of the chamber plate 222a. The valve hole 2231a is disposed at the convergence concave sheet 2232a and thus is sealed by the chamber plate convex portion 2225a. The discharge concave sheet 2233a correspondingly abuts against the convergence plate convex portion 2215a in the corresponding convergence plate assembly area 2213a of the convergence plate 221a, and thus seals the discharge outlet 2217a.

In this embodiment, in order to stably fix the valve sheet 223a between the chamber plate 222a and the convergence plate 221a without being shifted, a plurality of tenons 2227a are disposed on one surface of the chamber plate 222a. The valve sheet 223a is disposed on the surface of the chamber plate 222a, and the valve sheet 223a has positioning holes 2234a corresponding to the tenons 2227a. The convergence plate 221a is disposed on the valve sheet 223a, and the convergence plate 221a has mortises 2218a corresponding to the positioning holes 2234a. Therefore, when the valve sheet 223a is disposed between the chamber plate 222a and the convergence plate 221a, each of the tenons 2227a of the chamber plate 222a can be inserted into the corresponding positioning hole 2234a of the valve sheet 223a, and then be inserted into the corresponding mortises 2218a of the convergence plate 221a, so that the valve sheet 223a can be positioned without being shifted.

Please further refer to FIG. 8A, FIG. 8B, and FIG. 9A to FIG. 9E. In some embodiments, the gas transmission device 22b mentioned above may be a micro pump to control the gas flow in the wearable device. The gas transmission device 22b is disposed in the receiving trough 2222a of the chamber plate 222a so as to seal the confluence chamber 2223a and to transmit the gas to the confluence chamber 2223a as it is operated. The gas transmission device 22b is sequentially stacked by an inlet plate 221b, a resonance sheet 222b, a piezoelectric actuator 223b, a first insulation sheet 224b, a conductive sheet 225b, and a second insulation sheet 226b. The inlet plate 221b has at least one inlet hole 2211b, at least one convergence channel 2212b, and a convergence chamber 2213b. The inlet hole 2211b is configured to guide the gas to flow into the micro pump. The inlet hole 2211b correspondingly penetrates the inlet plate 221b and is in communication with the corresponding convergence channel 2212b, and the convergence channel 2212b is in communication with the convergence chamber 2213b, so that the gas guided by the inlet hole 2211b can be converged at the convergence chamber 2213b. In this embodiment, the number of the inlet holes 2211b and the number of the convergence channels 2212b are the same. The number of the inlet holes 2211b and the number of the convergence channels 2212b both may be four, but is not limited thereto. The four inlet holes 2211b are respectively in communication with the four convergence channels 2212b, and the four convergence channels 2212b are in communication with the convergence chamber 2213b.

The resonance sheet 222b may be attached to the inlet plate 221b, and the resonance sheet 222b has a perforation 2221b, a movable portion 2222b, and a fixed portion 2223b. The perforation 2221b is disposed at the center portion of the resonance sheet 222b and corresponds to the convergence chamber 2213b of the inlet plate 221b. The movable portion 2222b is disposed at the periphery of the perforation 2221b and corresponds to the convergence chamber 2213b of the inlet plate 221b. The fixed portion 2223b is disposed at the outer periphery of the resonance sheet 222b and attached to the inlet plate 221b.

The piezoelectric actuator 223b includes a suspension plate 2231b, an outer frame 2232b, at least one supporting element 2233b, a piezoelectric element 2234b, at least one gap 2235b, and a protruding portion 2236b. In some embodiments of the present disclosure, the suspension plate 2231b is in square shape. It is understood that, the reason why the suspension plate 2231b adopts the square shape is that, comparing with a circle suspension plate having a diameter equal to the side length of the square suspension plate 2231b, the square suspension plate 2231b has an advantage of saving electricity. The power consumption of a capacitive load operated under the resonance frequency may increase as the resonance frequency increases, and since the resonance frequency of a square suspension plate 2231*b* is much lower than that of a circular suspension plate, the power consumption of the square suspension plate 2231*b* is relatively low accordingly. Consequently, the square design of the suspension plate 2231*b* used in one or some embodiments of the present disclosure has the benefit of power saving. The outer frame 2232*b* is disposed around the periphery of the suspension plate 2231*b*. The at least one supporting element 2233*b* is connected between the suspension plate 2231*b* and the outer frame 2232*b* to provide a flexible support for the suspension plate 2231*b*. The piezoelectric element 2234*b* has a side length, and the side length of the piezoelectric element 2234*b* is shorter than or equal to a side length of the suspension plate 2231*b*. The piezoelectric element 2234*b* is attached to a surface of the suspension plate 2231*b* so as to drive the suspension plate 2231*b* to bend and vibrate when the piezoelectric element 2234*b* is applied with a voltage. The at least one gap 2235*b* is formed between the suspension plate 2231*b*, the outer frame 2232*b*, and the two adjacent supporting elements 2233*b*, and the at least one gap 2235*b* is provided for the gas to flow therethrough. The protruding portion 2236*b* is disposed on a surface of the suspension plate 2231*b* opposite to the surface of the suspension plate 2231*b* where the piezoelectric element 2234*b* is attached. In this embodiment, the protruding portion 2236*b* may be a protruding structure integrally formed with suspension plate 63*a* by a lithography process, and the protruding portion 2236*b* protrudes from the surface of the suspension plate 2231*b* opposite to the surface of the suspension plate 2231*b* where the piezoelectric element 2234*b* is attached.

Figure 9A:
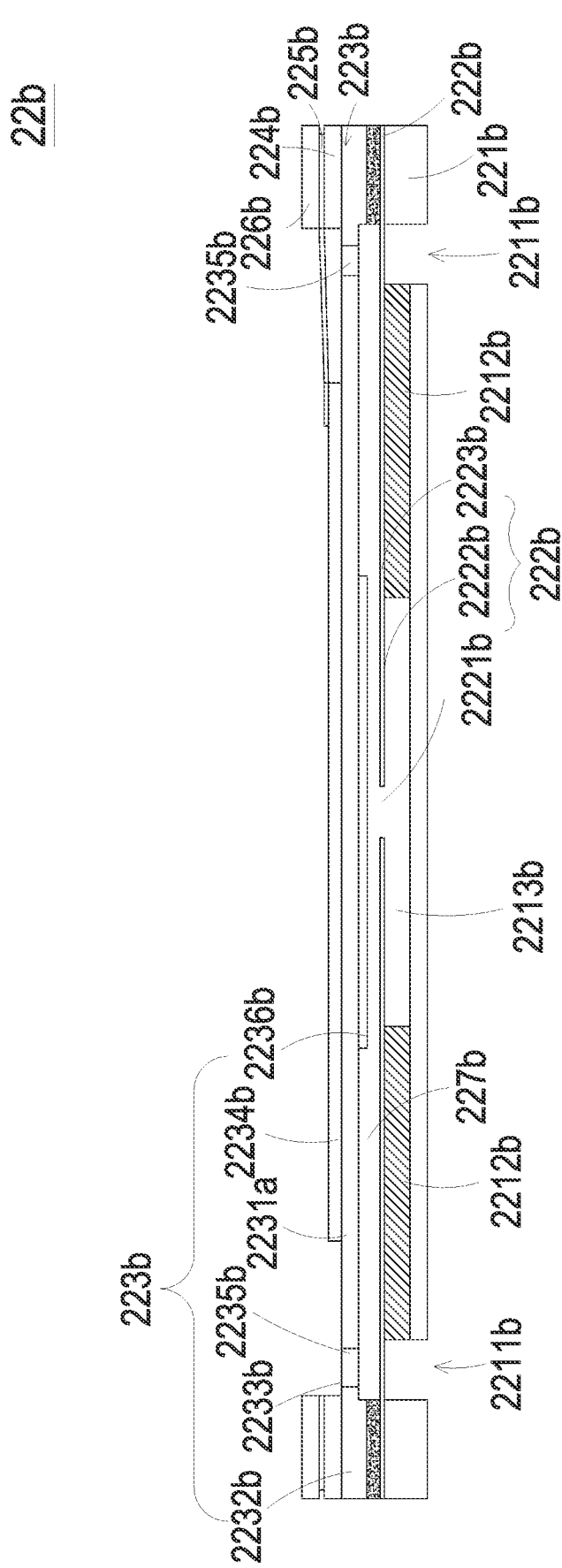
FIG. 9A illustrates a schematic cross-sectional view of the gas transmission device in the blood pressure measurement module according to the exemplary embodiment of the present disclosure.
Figure 9B:
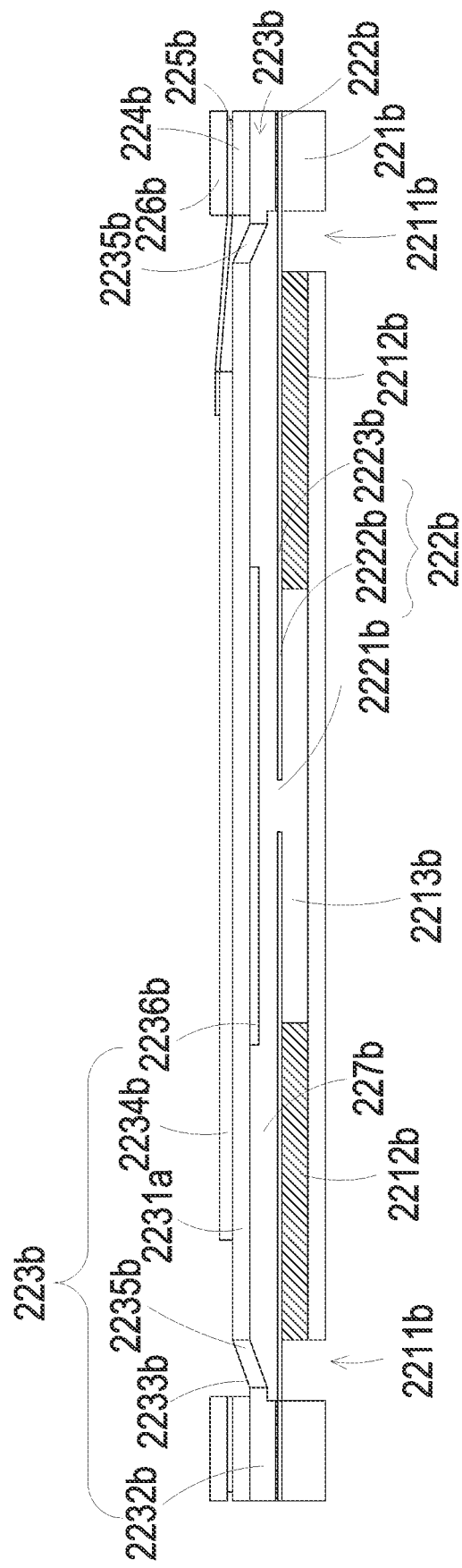
FIG. 9B illustrates a schematic cross-sectional view of the gas transmission device in the blood pressure measurement module according to another exemplary embodiment of the present disclosure.

The inlet plate 221*b*, the resonance sheet 222*b*, the piezoelectric actuator 223*b*, the first insulation plate 224*b*, the conductive plate 225*b*, and the second insulation plate 226*b* are sequentially stacked and assembled. A chamber space 227*b* needs to be formed between the suspension plate 2231*b* and the resonance sheet 222*b*. The chamber space 227*b* can be formed by filling a material, such as conductive adhesive, between the resonance sheet 222*b* and the outer frame 2232*b* of the piezoelectric actuator 223*b*, but not limited thereto. By filling a material between the resonance sheet 222*b* and the suspension plate 2231*b*, a certain distance can be maintained between the resonance sheet 222*b* and the suspension plate 2231*b* to form the chamber space 227*b*; thereby, the gas can be guided to flow more quickly. Furthermore, since an appropriate distance is maintained between the suspension plate 2231*b* and the resonance sheet 222*b*, the interference raised by the contact between the suspension plate 2231*b* and the resonance sheet 222*b* can be reduced, so that the noise generated thereby can be decreased as well. In other embodiments, the required thickness of the conductive adhesive to form the chamber space 227*b* between the resonance sheet 222*b* and the outer frame 2232*b* of the piezoelectric actuator 223*b* may be decreased by increasing the height of the outer frame 2232*b* of the piezoelectric actuator 223*b*. Accordingly, during assembling process of the gas transmission device 22*b*, the entire structure of the gas transmission device 22*b* would be indirectly affected under the hot pressing temperature and the cooling temperature of the conductive adhesive selected, thereby avoiding the situation that the actual spacing of the resulted chamber space 227*b* is affected by the thermal expansion and contraction of the filling material of the conductive adhesive, but embodiments are not limited thereto. Moreover, the size of the chamber space 227*b* also affects the transmission efficiency of the gas transmission device 22*b*. Therefore, it is important to maintain a fixed size of the chamber space 227*b* for the gas transmission device 22*b* to provide a stable transmission efficiency. Thus, as shown in FIG. 9B, in some other embodiments, the suspension plate 2231*b* can be extended outwardly a certain distance by stamping. The extension distance can be adjusted by at least one supporting element 2233*b* formed between the suspension plate 2231*b* and the outer frame 2232*b* so as to make the surface of the protruding portion 2236*b* of the suspension plate 2231*b* and the surface of the outer frame 2232*b* non-coplanar. That is, in this embodiment, the surface of the protruding portion 2236*b* is away from the surface of the outer frame 2232*b*, and thus is not coplanar with the surface of the outer frame 2232*b*. A few amount of filling material (such as the conductive adhesive) is applied onto the assembly surface of the outer frame 2232*b*, and the piezoelectric actuator 223*b* is assembled to the resonance sheet 222*b* by attaching the piezoelectric actuator 223*b* onto the fixed portion 2223*b* of the resonance sheet 222*b* through hot pressing. By stamping the suspension plate 2231*b* of the piezoelectric actuator 223*b* to form the chamber space 227*b*, the required chamber space 227*b* can be obtained by adjusting the extension distance of the suspension plate 2231*b* of the piezoelectric actuator 223*b* formed by stamping, which effectively simplifies the structural design of the chamber space 227*b*, and also simplifies the manufacturing process and shortens the manufacturing time of the piezoelectric actuator 223*b*. Moreover, the first insulation plate 224*b*, the conductive plate 225*b*, and the second insulation plate 226*b* are all thin sheets with a frame like structure. The first insulation plate 224*b*, the conductive plate 225*b*, and the second insulation plate 226*b* are staked sequentially on the piezoelectric actuator 223*b* to form the entire structure of the micro pump as the gas transmission device 22*b*.

Figure 9C:
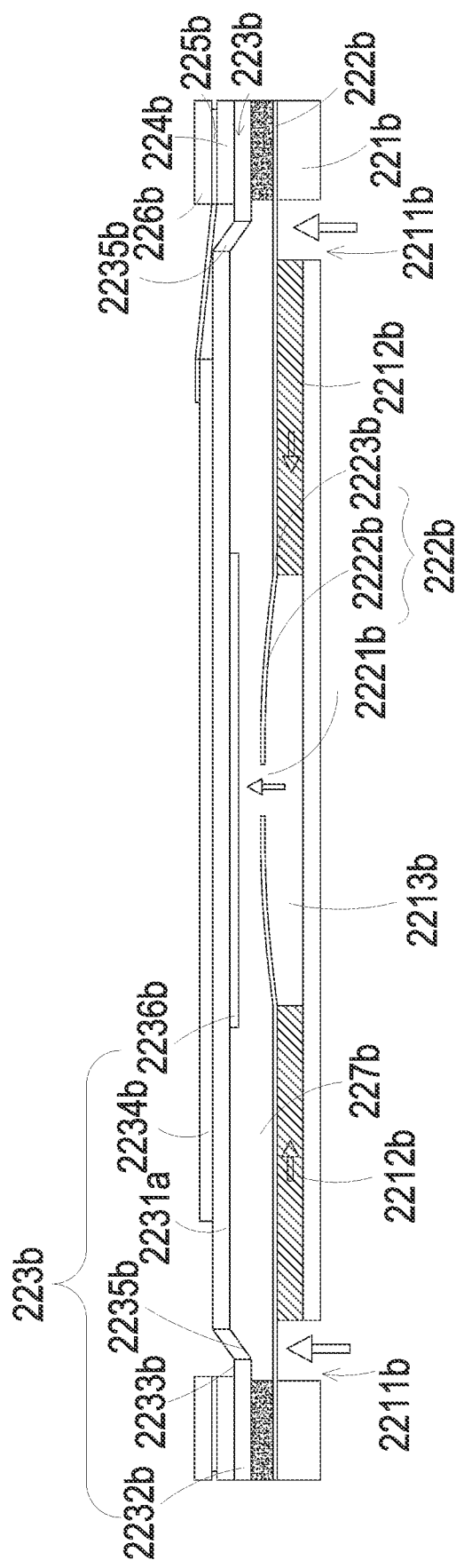
FIG. 9C to FIG. 9E illustrate schematic cross-sectional views showing the gas transmission device shown in FIG. 9A at different operation steps.
Figure 9D:
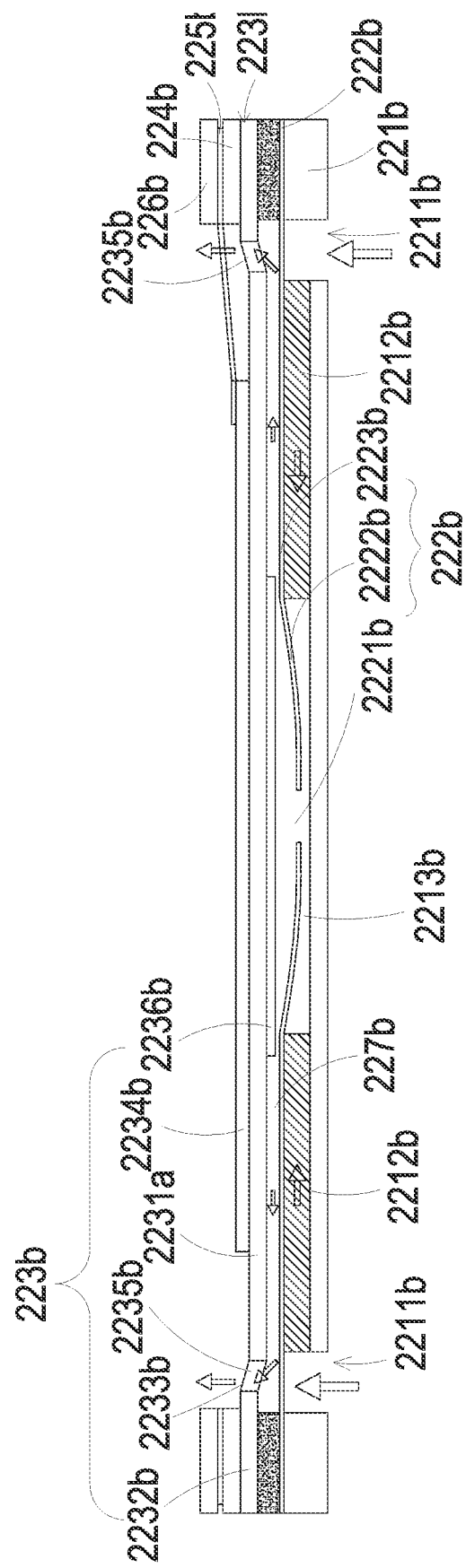
Figure 9E:
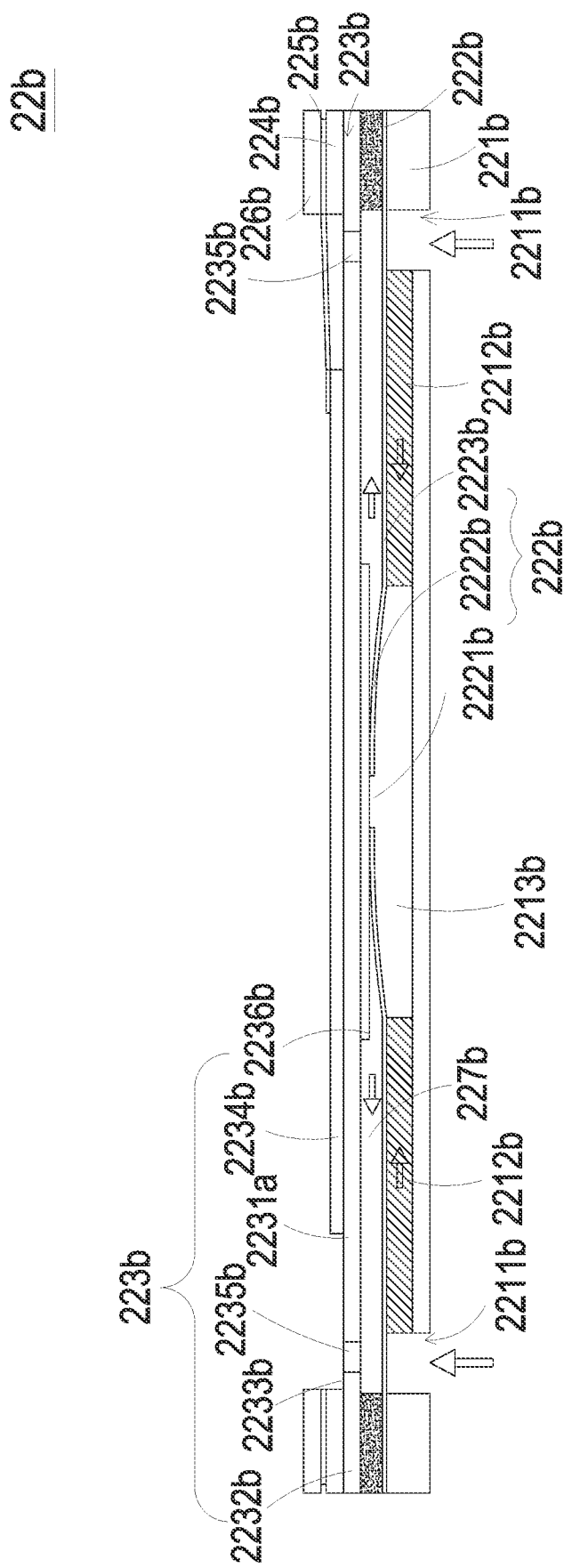

In order to understand the operation of the gas transmission device 22*b* in gas transmission, please refer to FIG. 9C to FIG. 9E. Please refer to FIG. 9C first, the piezoelectric element 2234*b* of the piezoelectric actuator 223*b* deforms after being applied with a driving voltage, and the piezoelectric element 2234*b* drives the suspension plate 2231*b* to move away from the resonance sheet 222*b*. Thus, the volume of the chamber space 227*b* is increased and a negative pressure is generated inside the chamber space 227*b*, thereby drawing the gas in the convergence chamber 2213*b* into the chamber space 227*b*. At the same time, owing to the resonance effect, the resonance sheet 222*b* is moved correspondingly, which also increases the volume of the convergence chamber 2213*b*. Furthermore, since the gas inside the convergence chamber 2213*b* is drawn into the chamber space 227*b*, the convergence chamber 2213*b* is in a negative pressure state as well. Therefore, the gas can be drawn into convergence chamber 2213*b* through the inlet hole 2211*b* and the convergence channel 2212*b*. Then, please refer to FIG. 9D. The piezoelectric element 2234*b* drives the suspension plate 2231*b* to move toward the resonance sheet 222*b*, thereby compressing the chamber space 227*b*. Similarly, since the resonance sheet 222*b* resonates with the suspension plate 2231*b*, the resonance sheet 222*b* is moved correspondingly, thereby pushing the gas in the chamber space 227*b* to be transmitted out of the chamber space 227*b* through the gap 2235*b* so as to achieve gas transmission. Last, please refer to FIG. 9E. When the suspension plate 2231*b* is moved resiliently to its original position, and the resonance sheet 222*b* is also moved away from the inlet plate 221b due to its inertia momentum, the resonance sheet 222b compresses the gas in the chamber space 227b and makes the gas in the chamber space 227b move toward the at least one gap 2235b and therefore the volume of the convergence chamber 2213b is increased. Accordingly, the gas can be drawn into the gas transmission device 22b continuously through the inlet holes 2211b and the convergence channels 2212b and converged at the convergence chamber 2213b. By continuously repeating the operation steps of the gas transmission device 22b shown in FIG. 9C to FIG. 9E, the gas transmission device 22b can make the gas continuously enter into the flow paths formed by the inlet plate 221b and the resonance sheet 222b from the inlet holes 2211b, thereby generating a pressure gradient and then transmitted outwardly through the gap 2235b. As a result, the gas can flow at a relatively high speed, by which the gas transmission device 22b can achieve gas transmission.

Moreover, the gas transmission device 22b can be fabricated by microelectromechanical surface micromachining techniques, by which the size of the gas transmission device 22b can be reduced so as to form a microelectromechanical systems (MEMS) micro pump.

It can be seen that, as shown in FIG. 5B, a plurality of the gas transmission device 22b is positioned in the receiving trough 2222a of the chamber plate 222a so as to seal the confluence chamber 2223a and operate to transmit the gas into the confluence chamber 2223a. When the gas transmission devices 22b operate, the gas transmission devices 22b guide the gas into the actuator 22 from the confluence chamber 2223a of the chamber plate 222a. Then, the gas flows into the flow guiding chamber 2221a through the plurality of the communication holes 2224a and the second communication hole 2226a. Accordingly, the valve sheet 223a is pushed to detach from the chamber plate convex portion 2225a and the valve sheet 223a is also pushed to contact against the convergence plate convex portion 2215a so as to seal the discharge outlet 2217a. Therefore, the gas passes through the valve hole 2231a of the valve sheet 223a and flows to the convergence trough 2214a of the convergence plate 221a through the flow guiding chamber 2221a, and the gas is converged at and discharged out from the convergence outlet 2211a through the guiding channel 2212a. Afterwards, the gas is converged at the expander 21 through the ventilation channel 24 so as to inflate the expander 21 to close-fit against the limb part 1A of the user (as shown in FIG. 6). Thus, the blood pressure measurement sensor 23 can measure the blood pressure in the cardiovascular system of the user.

Figure 5C:
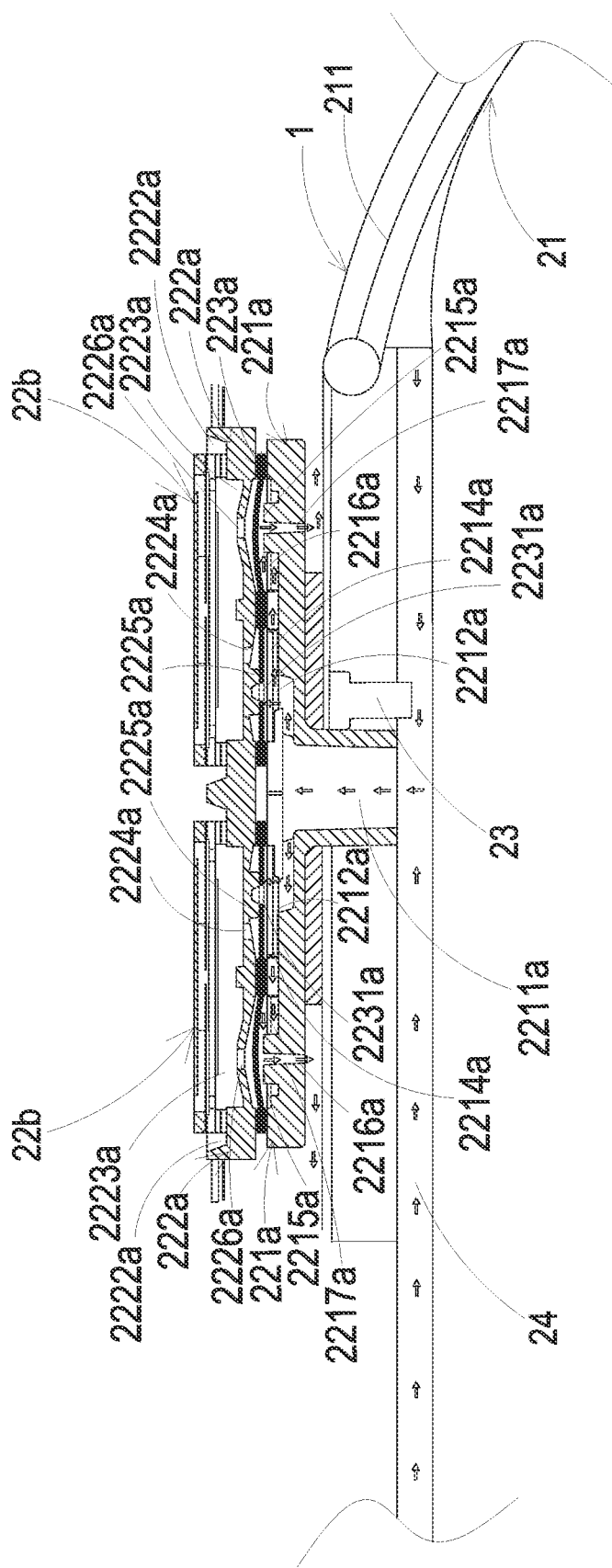
FIG. 5C illustrates a schematic cross-sectional view of the blood pressure measurement module during a gas discharging process (relieving process)

Then, as shown in FIG. 5C, when the plurality of the gas transmission devices 22b is not in operation, the gas in the convergence outlet 2211a of the convergence plate 221a can flow to the convergence trough 2214a through the flow guiding channel 2212a. The valve sheet 223a is pushed accordingly to contact against the chamber plate convex portion 2225a, and thus the valve hole 2231a of the valve sheet 223a is sealed. The gas further flows to the discharge trough 2216a through the flow guiding channel 2212a and pushes the portion of the valve sheet 223a corresponding to the discharge trough 2216a at the same time to detach from the convergence plate convex portion 2215a, so that the discharge outlet 2217a is opened. The gas is discharged out of the convergence plate 221a through the discharge outlet 2217a, by which the expander 21 achieves the gas discharging process.

The above mentioned sensor 3 may be a photo-plethysmography (PPG) sensor 31, which can perform a measurement on the limb part 1A of the user. Specifically, the PPG sensor 31 can generate a detection signal by directly receiving a reflected light emitted from a light source of the PPG sensor 31 to the skin tissue of the limb part 1A and reflected by the skin tissue, and accomplish a photo-plethysmography (PPG) measurement. The received detection signal may include health data information, such as heart rate data, ECG data, blood pressure data, etc. The photo-plethysmography (PPG) measurement may also be one way to obtain the blood pressure. However, it is understood that although this kind of measurement can be conducted any time, the received health data information is obtained under algorithm adjustment. As a result, the accuracy of this kind of blood pressure measurement is not enough as compared to the inflated measurement of the blood pressure measurement module 2 by inflating the expander 21 through the control of actuator 22 as shown in FIG. 5B to enable the blood pressure measurement sensor 23 to directly measure the blood pressure in the cardiovascular system of the user. Accordingly, the wearable device 10 of the present disclosure may transmit the accurate blood pressure value obtained by the blood pressure measurement module 2 through the inflated measurement to the processor 4. After this accurate blood pressure value is processed by the processor 4, the processed value can be served as a basis for the photo-plethysmography sensor 31 to perform initial calibration calculation, thereby achieving the accurate measurement of the blood pressure measurement through photo-plethysmography sensor 31. Namely, in this embodiment, when the photo-plethysmography sensor 31 performs the first measurement, the expander 21 is controlled by the actuator 22 to be inflated at first, so that the blood pressure sensor 23 can obtain the blood pressure in the cardiovascular system of the user through the inflated measurement. The obtained blood pressure value can be used as the basis for the calibration calculation of the photo-plethysmography sensor 31. Thus, the photo-plethysmography sensor 31 can adjust/compensate of the measured blood pressure value after each measurement; thereby, the photo-plethysmography sensor 31 can achieve the accurate measurement of the blood pressure.

To sum up, the present disclosure provides a wearable device for measuring the blood pressure in a cardiovascular system of a user, so that the user can carry the wearable device conveniently and can measure/monitor the blood pressure of a limb part of the user. Tightness between the user's skin and the wearable device can be adjusted through the expander and close-fits against the user's limb part during measuring the blood pressure. When the wearable device is not in the measuring mode, the expander would not be inflated and thus makes the wearable device of the present invention be worn more comfortable. Moreover, by using the photo-plethysmography (PPG) sensor to measure the blood pressure and take advantage of the blood pressure obtained by the blood pressure measurement module through the inflated blood pressure measurement method as a basis for the photo-plethysmography sensor to perform initial calibration calculation, accurate blood pressure value could be obtain by the photo-plethysmography sensor 31 at any time, and thus the industrial value of the blood pressure device of the present invention is quite high.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A wearable device capable of measuring a blood pressure of a cardiovascular system of a user, and the wearable device can be operable in a connected state and a disconnected state, the wearable device comprising:
   an attachment component capable of attaching the wearable device to a limb part of the user comprising a connecting mechanism used to determine whether the attachment component is in a connected configuration or in a disconnected configuration, wherein the attachment component is capable of being switched between the connected configuration and the disconnected configuration;
   a blood pressure measurement module comprising an expander, an actuator, and a blood pressure measurement sensor, wherein the expander is capable of being disposed on the limb part and contacting the user in a non-invasive manner, wherein the expander is in communication with the actuator through a ventilation channel, wherein the actuator comprises a valve device and at least one gas transmission device, and wherein the at least one gas transmission device is disposed on one side of the valve device, wherein the valve device comprises a convergence plate, at least one chamber plate, and at least one valve sheet, wherein the convergence plate has a convergence outlet and a plurality of guiding channels in communication with the convergence outlet, wherein a plurality of convergence plate assembly areas is defined on the convergence plate, wherein the convergence outlet is on the center of the convergence plate, wherein the convergence plate assembly areas are on a periphery of the convergence outlet, and each of the convergence plate assembly areas has a convergence trough, a convergence plate convex portion, a discharge trough, and a discharge outlet, wherein each of the guiding channels extends outward from the discharge outlet to communicate with the convergence trough in each of the plurality of convergence plate assembly areas, and each of the guiding channels is in communication between the convergence trough and the discharge trough in each of the plurality of convergence plate assembly areas, and wherein the convergence plate convex portion protrudes from the discharge trough and is surrounded by the discharge trough, and wherein the discharge outlet is disposed at a central portion of the convergence plate convex portion, wherein the convergence plate is disposed on each of the at least one chamber plate, and wherein a flow guiding chamber and a receiving trough are disposed in a portion of the at least one chamber plate corresponding to each of the plurality of convergence plate assembly areas of the convergence plate, wherein the flow guiding chamber and the receiving trough are respectively disposed on two opposite surfaces of the at least one chamber plate, and the flow guiding chamber corresponds to the convergence trough of the convergence plate and is in communication with the convergence trough, wherein a confluence chamber is disposed on a bottom of the receiving trough, and a plurality of communication holes are disposed on a bottom of the confluence chamber to communicate with the flow guiding chamber, and wherein a chamber plate convex portion is disposed in the flow guiding chamber and is surrounded by the communication holes, and wherein a second hole is disposed on a portion of the at least one chamber plate corresponding to the discharge trough of each of the plurality of convergence plate assembly areas of the convergence plate, and the second hole is in communication with the confluence chamber, wherein the at least one valve sheet is between the convergence plate and the at least one chamber plate, and the at least one valve sheet correspondingly abuts against the chamber plate convex portion in the at least one chamber plate, wherein a valve hole is disposed on the at least one valve sheet and corresponds to the chamber plate convex portion, so that the valve hole is sealed by the chamber plate convex portion, and wherein the at least one valve sheet abuts against the convergence plate convex portion in each of the plurality of convergence plate assembly areas of the convergence plate so as to seal the discharge outlet, and wherein the expander is capable of being controlled by the actuator to be inflated and enable the blood pressure measurement sensor to measure a blood pressure or a pulse in the cardiovascular system of the user;
   a sensor capable of detecting the limb part of the user;
   wherein the wearable device determines a timing when the attachment component is switched from the disconnected configuration to the connected configuration based on a condition of the connecting mechanism, and the wearable device is switched to the connected state from the disconnected state as the attachment component is determined to be connected to the wearable device; and
   wherein when the wearable device is operated in the disconnected state and determines that the attachment component is switched from the disconnected configuration to the connected configuration, the wearable device checks whether the sensor detects the limb part of the user.

2. The wearable device according to claim 1, wherein the sensor comprises a photo-plethysmographic sensor.

3. The wearable device according to claim 2, wherein the blood pressure measurement module drives the actuator to inflate the expander so as to measure the blood pressure or the pulse of the user, to generate a measured data, and to transmit the measured data to a processor; and wherein the measured data is processed by the processor so as to be served as a basis for the photo-plethysmography sensor to perform initial calibration calculation.

4. The wearable device according to claim 1, wherein the sensor comprises a proximity sensor.

5. The wearable device according to claim 1, wherein the wearable device is configured to be operated in the connected state when the attachment component is attached to the limb part of the user.

6. The wearable device according to claim 1, wherein the wearable device is configured to be operated in the disconnected state when the attachment component is not attached to the limb part of the user.

7. The wearable device according to claim 1, further comprising a first contact and a second contact, wherein the wearable device determines whether the attachment component is in the disconnected configuration or in the connected configuration by measuring the conductivity coefficient between the first contact and the second contact.

8. The wearable device according to claim 1, wherein the attachment component comprises a first portion and a second portion, wherein
the first portion is coupled to the second portion by a first magnetic element and a second magnetic element when the attachment component is in the connected configuration;
the first portion is detached from the second portion by decoupling between the first magnetic element and the second magnetic element when the attachment component is in the disconnected configuration; and
the wearable device measures a magnetic field of the first magnetic element and a magnetic field of the second magnetic element by a Hall-effect sensor so as to determine whether the attachment component is in the connected configuration or in the disconnected configuration.

9. The wearable device according to claim 1, wherein when the gas transmission device is not in operation, gas at the convergence outlet of the convergence plate is capable of being guided into the convergence trough through each of the guiding channels, whereby the gas pushes the valve sheet to move, so that the valve hole of the valve sheet abuts against the chamber plate convex portion so as to be sealed, and the gas further flows into the discharge trough through each of the guiding channels to push the valve sheet corresponding to the discharge trough to detach from the convergence plate convex portion, thereby opening the discharge outlet, and the gas is discharged out of the convergence plate from the discharge outlet, thereby achieving a pressure-releasing procedure.

10. The wearable device according to claim 1, wherein the gas transmission device is a micro pump comprising:
an inlet plate having at least one inlet hole, at least one convergence channel, and a convergence chamber, wherein the at least one inlet hole is configured to introduce gas into the micro pump, and wherein the at least one inlet hole correspondingly penetrates the inlet plate and is in communication with the at least one convergence channel, and the at least one convergence channel is in communication with the convergence chamber, so that the gas introduced by the at least one inlet hole is converged at the convergence chamber;
a resonance sheet attached to the inlet plate, wherein the resonance sheet has a perforation, a movable portion, and a fixed portion, and wherein the perforation is disposed at a center portion of the resonance sheet and corresponds to the convergence chamber of the inlet plate, the movable portion is disposed around a periphery of the perforation and corresponds to the convergence chamber, and the fixed portion is disposed around a periphery of the resonance sheet and is attached to the inlet plate; and
a piezoelectric actuator attached to the resonance sheet, wherein the piezoelectric actuator is correspondingly disposed to the resonance sheet;
wherein a chamber space is formed between the resonance sheet and the piezoelectric actuator, so that when the piezoelectric actuator is driven, the gas is guided into the micro piezoelectric pump through the at least one inlet hole of the inlet plate, is converged at the convergence chamber via the at least one convergence channel, flows through the perforation of the resonance sheet, and then is transmitted owing to a resonance effect between the piezoelectric actuator and the movable portion of the resonance sheet.

11. The wearable device according to claim 10, wherein the piezoelectric actuator comprises:
a suspension plate in square shape and capable of bending and vibrating;
an outer frame disposed around a periphery of the suspension plate;
at least one supporting element connected between the suspension plate and the outer frame to provide a flexible support for the suspension plate; and
a piezoelectric element having a side length, wherein the side length of the piezoelectric element is smaller than or equal to a side length of the suspension plate, and the piezoelectric element is attached to a surface of the suspension plate so as to drive the suspension plate to bend and vibrate when the piezoelectric element is applied with a voltage.

12. The blood pressure device according to claim 10, wherein the piezoelectric actuator comprises:
a suspension plate in square shape and capable of bending and vibrating;
an outer frame disposed around a periphery of the suspension plate;
at least one supporting element connected between the suspension plate and the outer frame to provide a flexible support for the suspension plate, wherein a surface of the suspension plate and a surface of the outer frame are non-coplanar, so that a chamber space is formed between the surface of the suspension plate and the resonance sheet; and
a piezoelectric element having a side length, wherein the side length of the piezoelectric element is smaller than or equal to a side length of the suspension plate, and the piezoelectric element is attached to a surface of the suspension plate so as to drive the suspension plate to bend and vibrate when the piezoelectric element is applied with a voltage.

13. The wearable device according to claim 1, wherein the gas transmission device is a microelectromechanical systems micro pump.

* * * * *